(12) United States Patent
Belly et al.

(10) Patent No.: US 7,267,950 B2
(45) Date of Patent: Sep. 11, 2007

(54) RAPID EXTRACTION OF RNA FROM CELLS AND TISSUES

(75) Inventors: Robert Belly, Webster, NY (US);
Jacqueline Toner, Penfield, NY (US);
John Backus, Pittsford, NY (US)

(73) Assignee: Veridex, LCC, Raritan, NJ (US)

( * ) Notice: Subject to any disclaimer, the term of this patent is extended or adjusted under 35 U.S.C. 154(b) by 326 days.

(21) Appl. No.: 10/427,217

(22) Filed: May 1, 2003

(65) Prior Publication Data

US 2004/0219534 A1 Nov. 4, 2004

(51) Int. Cl.
*C12Q 1/68* (2006.01)
(52) U.S. Cl. .................................................. 435/6
(58) Field of Classification Search ................ None
See application file for complete search history.

(56) References Cited

U.S. PATENT DOCUMENTS

| | | | |
|---|---|---|---|
| 3,389,133 A | 6/1968 | Gutcho | |
| 4,843,155 A | 6/1989 | Chomczynski | |
| 5,010,183 A | 4/1991 | Macfarlane | |
| 5,155,018 A | 10/1992 | Gillespie | |
| 5,346,994 A | 9/1994 | Chomczynski | |
| 5,438,128 A | 8/1995 | Nieuwkerk et al. | |
| 5,620,852 A | 4/1997 | Lin et al. | |
| 5,643,767 A | 7/1997 | Fischetti et al. | |
| 5,654,179 A | 8/1997 | Lin | |
| 5,777,099 A | 7/1998 | Mehra | |
| 5,786,208 A | 7/1998 | Clark et al. | |
| 5,945,515 A | 8/1999 | Chomczynski | |
| 5,973,137 A | 10/1999 | Heath | |
| 6,204,375 B1 | 3/2001 | Lader | |
| 6,218,531 B1 | 4/2001 | Ekenberg | |
| 6,248,535 B1 | 6/2001 | Danenberg et al. | |
| 6,428,963 B2 | 8/2002 | Danenberg et al. | |
| 2002/0009738 A1 | 1/2002 | Houghton et al. | |
| 2002/0009794 A1 | 1/2002 | Danenberg et al. | |
| 2002/0009795 A1 | 1/2002 | Danenberg et al. | |
| 2002/0081619 A1 | 6/2002 | Bastian et al. | |

FOREIGN PATENT DOCUMENTS

| WO | WO95/28409 | 10/1995 |
|---|---|---|
| WO | WO98/45311 | 10/1998 |
| WO | WO 02/057289 A1 | 7/2002 |
| WO | WO 02/070751 A1 | 9/2002 |

OTHER PUBLICATIONS

Johansson et al., "Quantitative Analysis of Tyrosinase Transcripts in Blood," Clinical Chemistry, 2000, vol. 46, No. 7, pp. 921-927.*
Ultraspec-3 RNA, "Isolation system for liquid samples," Product description, published and available as of Feb. 1999.*
European Search Report, dated Jul. 20, 2005, for European Appln. No. EP04252529.
Ambion, Inc., "RNAqueous TM-4PCR Instruction Manual, Version 0204", RNAQUEOUSTM-4PCR, Apr. 2002, pp. 1-29.
Quiagen, Inc., "RNeasy Mini Handbook", RNeasy, Mini, Jun. 2001, pp. 1-112.
"Maximize your RNA yield: What yield to expect", Technotes International Edition, vol. 8, No. 3, May 2001, pp. 1, 13-14, Austin Texas.

* cited by examiner

*Primary Examiner*—Young J. Kim
(74) *Attorney, Agent, or Firm*—Todd Volyn

(57) ABSTRACT

A method of extracting RNA from biological systems (cells, cell fragments, organelles, tissues, organs, or organisms) is presented in which a solution containing RNA is contacted with a substrate to which RNA can bind. RNA is withdrawn from the substrate by applying negative pressure. No centrifugation step exceeds thirty seconds. Preferably, the RNA is diluted prior to filtration and one or more wash steps can be used to remove interferents. In one such method, except for DNA shearing and drying steps, centrifugation is not undertaken during the extraction step.

3 Claims, 2 Drawing Sheets

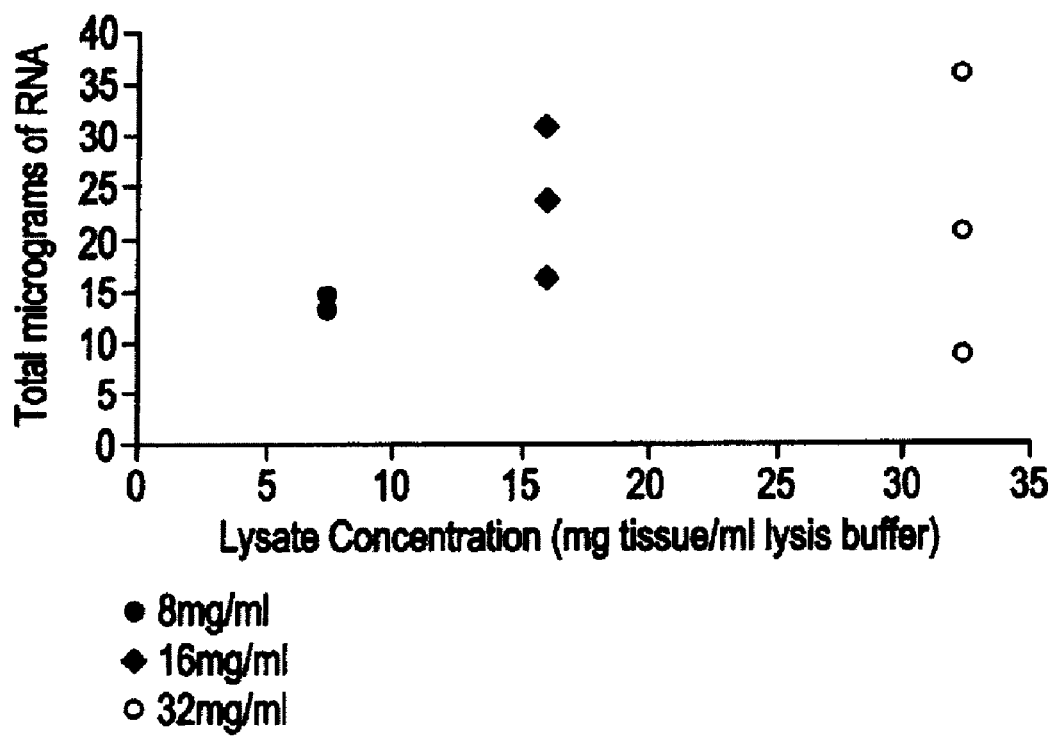

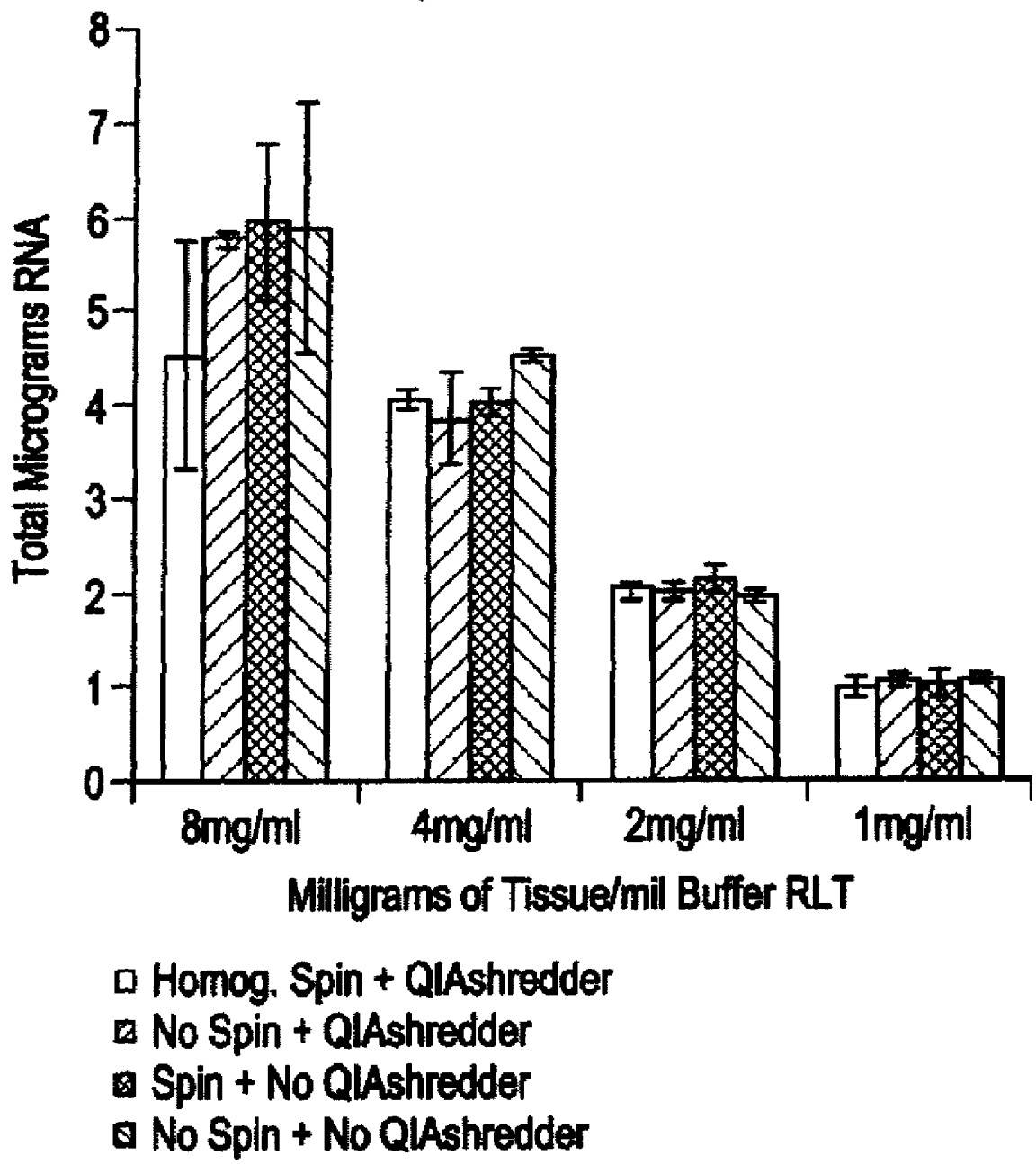

RAPID EXTRACTION OF RNA FROM CELLS AND TISSUES

BACKGROUND

The invention relates to the extraction of RNA for use in, among other things, in vitro diagnostics.

As a result of recent progress in genomic technology and bioinformatics, new gene expression markers useful as diagnostic, prognostic and therapeutic indicators for cancer and other diseases are rapidly being discovered. To evaluate and apply these markers as in vitro diagnostic tests, there is a need for a rapid, sensitive, and easy-to-use method of RNA extraction from cells, tissues, and other biological components.

In oncology, rapid intra-operative molecular testing may be used to more sensitively detect surgical margins, lymph node or other sites of metastases, and to confirm the presence or absence of cancer in a tissue. To impact surgical care, diagnostic results useful in the intraoperative setting must be made available to the treating surgeon during the time that the patient is in the operating room, generally about 45 min. To allow time for reverse transcription and subsequent amplification and detection of molecular markers, amplifiable RNA from cells and tissues must be extracted and purified within a few minutes.

Several different approaches have been developed for the isolation and purification of RNA from cells and tissues. These include membrane-based methods, solution based methods, and magnetic based methods. Solution based methods generally require at least 90 minutes to perform and involve the use of toxic solvents. Magnetic particle methods have been developed but require at least 45 min to perform.

Kits for performing membrane based RNA purification are commercially available from several vendors. Generally, kits are-developed for the small-scale (30 mg or less) preparation of RNA from cells and tissues (eg. QIAGEN RNeasy Mini kit), for the medium scale (250 mg tissue) (eg. QIAGEN RNeasy Midi kit), and for the large scale (1 g maximum) (QIAGEN RNeasy Maxi kit). Unfortunately, currently available membrane based RNA extraction and purification systems require multiple steps, and may be too slow for intra-operative diagnostic applications.

Accordingly, a more rapid membrane-based RNA extraction method is needed particularly for use in intraoperative diagnostic applications.

SUMMARY OF THE INVENTION

The invention is a method of extracting RNA from biological systems (cells, cell fragments, organelles, tissues, organs, or organisms) in which a solution containing RNA is contacted with a substrate to which RNA can bind. RNA is withdrawn from the substrate by applying negative pressure. No centrifugation step exceeds thirty seconds. Preferably, the RNA is diluted prior to filtration and one or more wash steps can be used to remove interferents. In a further embodiment, except for DNA shearing and drying steps, centrifugation is not undertaken during the extraction step.

In a further aspect of the invention, cells without RNA of interest are removed from those with RNA of interest. The cells containing RNA of interest are then lysed and the lysate is contacted with a substrate containing or to which is affixed a material that binds (is adherent to) RNA. Negative pressure is applied to substrate for a period preferably less than 15 seconds and interferences are removed from the substrate without the application of centrifugation.

In a yet further aspect of the invention, a method of extracting RNA from biological systems has the following steps.
(a) obtaining a sample containing cells from the biological system,
(b) optionally, removing from the sample, cells without RNA of interest to produce a working sample,
(c) lysing the cells containing RNA that is of interest and producing a homogenate of them,
(d) diluting the homogenate,
(e) contacting the wetted, homogenized working sample with a substrate containing, or to which is affixed, a material to which RNA binds,
(f) allowing the sample to bind to the substrate,
(g) removing contaminants and interferents,
(h) drying the substrate, and
(i) eluting RNA from the substrate;
the method is conducted in less than 8 minutes.

BRIEF DESCRIPTION OF THE DRAWINGS

FIG. 1 is a graphical representation of RNA recovery in dilution experiments described in Example 6.
FIG. 2 is a graphical representation of RNA recovery in dilution experiments described in Example 7.

DETAILED DESCRIPTION OF THE INVENTION

The biological systems of the invention are organelles, cells, cell fragments, tissue, organs, or organisms. The solutions that contain RNA of interest can be obtained from any fluid found in or made from the biological system.

The successful isolation of intact RNA generally involves at least four steps: effective disruption of cells or tissue, denaturation of nucleoprotein complexes, inactivation of endogenous ribonuclease (RNAase) and removal of contaminating DNA and protein.

Depending on the sample containing the RNA of interest (i.e., the RNA whose marker(s) will be assayed) it may be desirable to remove cells without RNA of interest Removing cells without RNA of interest is preferably done by lysing them and removing the lysate from the solution. When working with whole blood, it is the red blood cells that make up the bulk of the cells present without RNA of interest since they are present in large quantities and are not nucleated. The red blood cells are very susceptible to hypotonic shock and can thus be made to burst in the presence of a hypotonic buffer. Lysing reagents are well known in the art and can include solutions containing ammonium chloride-potassium or ammonium oxalate among many others.

For tissues, commercial RNA extraction kits such as those offered by Qiagen, lysing buffers are used. Preferably, these contain a guanidine-thiocyante (GTC) solution and one or more surfactants such as sodium dodecylsulfate as well as a strong reducing agent such as 2-mercaptoethanol to inhibit or inactivate ribonucleases (RNAases). GTC has particularly useful disruptive and RNA protective properties. The GTC/surfactant combination acts to disrupt nucleoprotein complexes, allowing the RNA to be released into solution and isolated free of protein. Dilution of cell extracts in the presence of high concentrations of GTC causes selective precipitation of cellular proteins to occur while RNA remains in solution. Most preferably, RLT buffer (sometimes referred to as lysis or homogenization buffer) is used as it is commercially available from Qiagen and a component of their RNA extraction kits. Lysis and removal of cells and undesirable cellular components can be aided by mechanical disruption as with a homogenizer, bead mixer, mortor and pestle, hand grinder, or other similar device.

The distribution of metastases and micrometastases in tissues is not uniform in nodes or other tissues. Therefore, a sufficiently large sample should be obtained so that metastases will not be missed. One approach to sampling issue in the present method is to homogenize a large tissue sample, and subsequently perform a dilution of the well mixed homogenized sample to be used in subsequent molecular testing.

A dilution step after homogenization and prior to the addition of the homogenate to the RNA binding step (as described below) is particularly advantageous. The dilution step involves adding a diluent that is a reagent that dilutes the tissue homogenate without contributing to RNA instability. Preferably, it is a reagent such as the RLT buffer described above. Preferably, the homogenate is diluted at between 8 and 2 mg of homogenate per ml of diluent. More preferably, the homogenate is diluted at between about 4 and 2 mg /ml. Most preferably, the homogenate is diluted at about 4 mg/ml.

Such a dilution step allows for fast filtering, as for example, through a spin column. It also eliminates or greatly reduces clogging in spin columns, eliminates the need for subsequent large volumes of homogenization buffer, eliminates the need for subsequent centrifugation steps, and can eliminate the need for passage of the sample through a shredding column or device. Ultimately, such a dilution step renders RNA extraction easier and results in a more standardized protocol.

Cells, debris or non-RNA materials are generally removed through one or more wash steps, and the purified RNA is then extracted as, for example, by elution from a substrate-containing column.

The RNA is selectively precipitated out of solution with ethanol and bound to a membrane/substrate such as the silica surface of the glass fibers. The binding of RNA to the substrate occurs rapidly due to the disruption of the water molecules by the chaotropic salts, thus favoring absorption of nucleic acids to the silica. The bound total RNA is further purified from contaminating salts, proteins and cellular impurities by simple washing steps. Finally, the total RNA is eluted from the membrane by the addition of nuclease-free water.

Several kits for RNA extraction from tissues based on "spin column" purification have been commercialized. All are compatible with the method of this invention. These kits include those sold by Invitrogen Corp. (Carlsbad, Calif.), Stratagene (La Jolla, Calif.), BDBiosciences Clontech (Palo Alto, Calif.), Sigma-Aldrich (St. Louis, Mo.), Ambion, Inc. (Austin, Tex.), and Promega Corp. (Madison, Wis.). Typically, these kits contain a lysis binding buffer having a guanidinium salt (4.0M or greater) in buffer, wash solutions having different dilutions of ethanol in buffer either in the presence or absence of a chaotropic salt such as guanidinium, and an elution buffer, usually nuclease-free distilled water. Typically, contain reagents such as:

Lysis/Binding buffer (4.5M guanidinium-HCl, 100 mM sodium phosphate),
Wash buffer I (37% ethanol in 5M guanidine-HCL, 20 mM Tris-HCL),
Wash buffer II (80% ethanol in 20 mM NaCl, 2 mM Tris-HCl),
Elution buffer, and
Nuclease-free sterile double distilled water.

The use of a substrate to which RNA binds or to which a material is bound that RNA binds to is what distinguishes this method as a membrane-based RNA extraction method. RNA binds to such material by any chemical or physical means provided that the RNA is easily released by or from the material, as for example, by elution with a suitable reagent. Numerous substrates are now commonly used in membrane-based methods. Macherey-Nagel silica gel membrane technology is one such method and is described in EP 0496822 which is incorporated herein by reference. Essentially, RNA is adsorbed to a silica-gel membrane. High concentrations of chaotropic salts are included in the reagents which remove water from hydrated molecules in solution; polysaccharides and proteins do not adsorb and are removed. After a wash step pure RNA is eluted under low-salt conditions.

Ion exchange resins are also frequently used as substrates for RNA extraction in membrane-based systems. Qiagen, for example, has a commercially available anion exchange resin in which a low salt concentration is employed when the working sample is exposed to the substrate (binding), a high salt concentration is used during washing of the RNA, and precipitation is via an alcohol. The resin is silica-based with a high density of diethylaminoethyl groups (DEAE). Salt concentration and pH are controlled by the addition and use of the buffers for use with the substrate. An example of such an ion exchange resin available from Qiagen is as follows:

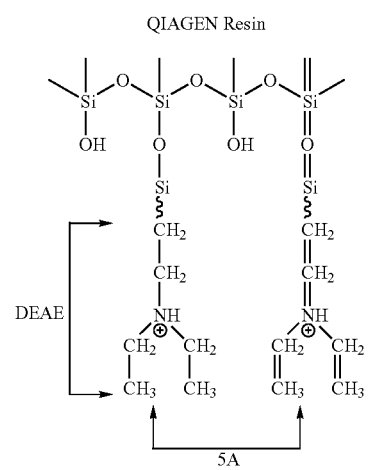

The most preferred substrate is a simple silica gel as follows:

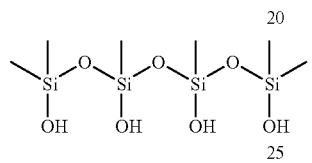

In the presence of binding buffers, nucleic acids adsorb to the silica gel. In the preferred embodiments of this invention, the substrate is contained in a vessel such as a column. Most preferably, these columns are commercially obtained such as the "RNeasy" columns available from Qiagen, GbH.

The preferred method for extracting and purifying RNA from tissue samples less than 30 mg applying the reagents contained in the RNeasy Mini kit available from QIAGEN, GbH to the methods described herein. For extraction of larger amounts of RNA from larger tissue samples, the method described below can be readily scaled by. one of ordinary skill using, among other reagent configurations, kits commercially available as. QIAGEN RNeasy MIDI or QIAGEN RNeasy MAXI kits from QIAGEN, GbH.

When using such kits, the preferred method according to the instant invention is as follows:

For starting tissues of less than 20 mg, 350 to 600 ul of Homogenization Buffer (preferably, RLT buffer obtained in the kit from Qiagen) is added to the tissue, and for 20-30 mg of tissue, 600 ul of Buffer is preferably added. The amount of Homogenization buffer can be scaled depending upon the tissue sample. Tissue or cells are then disrupted by one of the following methods including but not limited to rotor-stator homogenizers, bead mixers, mortor and pestle, and by hand grinders. Homogenization is usually done by the use of a disposable tissue grinder (VWR Scientific, cat 15704-126 or 15704-124) when manual cell and tissue disruption is undertaken. More preferably, homogenization is conducted through the use of a mechanical device made for this purpose such as the PCR Tissue Homogenization Kit commercially available from Omni International (Warrenton, Va.).

Homogenization time is typically about one minute and preferably as soon as tissue is visibly homogenized.

It may be desirable, as with dense tissue samples, to decease the viscosity of the sample. Most preferably, this is done by the addition of homogenization buffer to homogenate (8 mg homogenate/ml buffer to 2 mg/ml). It can also be done with one or more passes through a needle (preferably about 20 guage) fitted to an RNAase-free syringe, or with a device such as a QIA shredder column used with centrifugation.

1 volume of 70% ethanol is preferably added to the cleared lysate, and mixed by pipetting.

Up to about 700 ul of the sample prepared thus far is applied to a vessel housing the RNA binding matrix (preferably, an RNeasy silica gel mini column from the Qiagen kit) and/or discarded by filtration (as opposed to centrifugation) and preferably the application of vacuum. Preferably vacuum is applied at about 11 to 13 psi (as is the case for all vacuum steps) for about 15 to 60 sec. Here as in all steps in which vacuum is applied, the time in which it is applied can be decreased with an increase in vacuum pressure provided that it does not exceed the capacity of the matrix to withstand such pressure.

Wash Buffer (preferably about 700 µl of RW1 buffer from the Qiagen kit) is added to the vessel housing the RNA binding matrix (preferably, RNeasy column) and the flow-through fluid is removed/and or discarded by filtration preferably through filtration and preferably the application of vacuum and collection tube are then removed and/or discarded.

A second Wash Buffer (preferably about 500 ul of RPE buffer from the Qiagen kit) is pipetted on to the column. The tube is closed gently and the flow-through is removed and/or discarded by filtration and preferably the application of vacuum.

Optionally, wash buffer (preferably about 500 ul of RPE buffer) can be added again to the vessel (preferably, Rneasy column); The tube is gently closed and the substrate/membrane is dried. The vessel is preferably placed in a new 2 ml collection tube and centrifuged (preferably, for 1 minute at about 8,000 g).

For elution, the vessel is preferably transferred to a new 1.5 ml collection tube and 30-50 ul Rnase-free water is pipetted directly onto the substrate/membrane. The tube is closed gently and centrifuged (preferably at about 10,000 RPM for about 30 seconds) to elute the RNA. If the RNA yield is expected to exceed 30 ug, the steps of this paragraph are preferably repeated during elution.

The RNAeasy protocol for isolation of total RNA from animal tissue (QIAGEN RNAeasy Handbook, June 2001) requires total centrifuation times of at least 6 min 45 sec and 8 min 45 sec when acceleration and deceleration time for the centrifuge is included. In comparison, total time for all filtration and centrifugation steps in the rapid method of the instant invention is 2 min and 15 sec, and 3 min when acceleration and deceleration of the centrifuge are included. In addition about 30 sec to 1 min for tissue homogenization and about 45 sec to 1 min for sample manipulation (including dilution and mixing steps) are common to the method of the invention and the method of the prior art.

Thus, the total time for the method of this invention is less than eight minutes, preferably, less than six minutes. A total extraction time of five minutes is particularly desirable and attainable where the sample is a single lymph node.

A vacuum manifold such as a QIA vac 24 Vacuum Manifold is preferably used for convenient vacuum processing of spin columns in parallel. Samples and wash solutions are drawn through the column membranes by vacuum instead of centrifugation, providing greater speed, and reduced hands-on time in the extraction and purification of RNA from cells and tissues.

This method can be used to extract RNA from plant and animal cells as well as bacteria, yeast, plants, and filamentous fungi with an appropriate disruption method.

EXAMPLES

Real-Time PCR

Examples in the present invention are based on the use of real-time PCR. In real-time PCR the products of the polymerase chain reaction are monitored in real-time during the exponential phase of PCR rather than by an end-point measurement. Hence, the quantification of DNA and RNA is much more precise and reproducible. Fluorescence values are recorded during every cycle and represent the amount of product amplified to that point in the amplification reaction. The more templates present at the beginning of the reaction, the fewer number of cycles it takes to reach a point in which the fluorescent signal is first recorded as statistically significant above background, which is the definition of the (Ct) values. The concept of the threshold cycle (Ct) allows for accurate and reproducible quantification using fluorescence based RT-PCR. Homogeneous detection of PCR products can be performed using many different detection methods including those based on double-stranded DNA binding dyes (e.g., SYBR Green), fluorogenic probes (e.g., Taq Man probes, Molecular Beacons), and direct labeled primers (e.g., Amplifluor primers).

Example 1

Short Centrifugation Time

In this example, two breast lymph nodes were purchased from Asterand Inc. (Detroit Mich.).

One node was confirmed as cancer positive by pathology (ALNC1) and a second node was negative for cancer (ALNN1).

As a control, 30 mg of tissue from each node was extracted and purified using the QIAGEN RNeasy Mini Procedure as recommended by the manufacturer and as described above. Triplicate extractions from a single homogenate were performed on each sample. In a similar manner, triplicate 30 mg sections were processed with the Qiagen RNeasy Mini Procedure, except that after the final addiiton of RPE wash buffer, each centrifugation step was reduced to 30 sec. All centrifugation steps were performed on an Eppendorf model 5415C microcentrifuge (Brinkman, Instruments, Inc, Westbury N.Y.).

The RNA extracted from each node was analyzed spectrophotometrically at 260 and 280 nm on a Hewlitt-Packard HP8453 UV-Visible Spectroscopy System (Waldbronn Germany), and the total RNA yield was determined at 260 nm and RNA quality was judged based on the 260 nm/280 nm ratio for each sample.

All reagents including primers were purchased from Invitrogen Corp, Carlsbad Calif. except where noted below.

The resulting RNA was transcribed to make cDNA copies as follows. A stock solution of 5 μL of anchored Oligo dT23, 5 μL of 10 mM each dNTP, and RNAase-treated water (Sigma Chemical Co, St. Louis, Mo.) to 50 μL was made, and 2.5 ug of RNA was added and the solution was heated to 70 C for 5 min, and then placed on ice. Then 38 μL of a solution of 20 μL of 5× Superscript First-Strand Buffer, 10 μL of 0.1M Dithiothreitol, 3 μL of a solution of 40 U/μL Rnasin (Promega Corp, Madison Wis.) and 5 μL of 200 U/μL Superscript II reverse transcriptase and RNAase free water (Sigma Chemical Co, St Louis, Mo.) to a volume of 38 μL was added. The tube was incubated at 42 C for 50 min, and then 40 μL of 0.5M NaOH was added and the tube was incubated at 70 C for 5 min. Twenty μL of 1M Tris-HCl buffer, pH 7.0, was added, followed by 90 ul of RNAase free water. Assuming complete conversion of RNA to cDNA, and a conversion factor of 1ug equal to 100,000 cell equivalents (CE), a concentration of 1000 CE/μL in 80 mM Tris buffer was used for all subsequent real-time PCR assays.

The following protocol based on SYBR green detection in a real-time PCR format was used for the quantitative detection of the housekeeping gene porphobilinogen deaminase (PBGD, Seq. ID No. 20), as well as for the breast cancer specific genes mammaglobin (Seq ID No. 17) and prolactin-inducibleprotein (PIP, Seq ID No. 18). A stock master mix solution of 10 μL of 10×PCR Buffer#1 (Applied Biosystems, Inc, Foster City Calif.), 0.1 μL of 10M $MgCl_2$, 2 μL of 10 mM of dNTP's, 1 μL of 100× SYBER Green solution (Sigma Chemical Co, St. Louis, Mo.), 2 μL of each primer from a 5 uM stock in TE buffer, and 0.75 μL of Taq/anti-Taq antibody mix, and RNAase free water to 94 μL. The Taq DNA polymerase and anti-Taq antibodies were mixed and incubated for 10-15 minutes prior to the addition of the other reaction components. One μL of cDNA (1,000 CE) was added to each well along with 49 ul of the above master mix solution.

The following primer pairs were used: For PBGD, SEQ ID NO. 1 and SEQ ID NO. 2; for mammaglobin, SEQ ID NO. 3 and SEQ ID NO. 4; and for PIP, SEQ ID NO. 5 and SEQ ID NO. 6.

```
SEQ ID NO. 1  ATGACTGCCT TGCCTCCTCA GTA (PBGD)

SEQ ID NO. 2  GGCTGTTGCT TGGACTTCTC TAAAGA (PBGD)

SEQ ID NO. 3  CAAACGGATG AAACTCTGAG CAATGTTGA
              (MAMAGLOBIN)

SEQ ID NO. 4  TCTGTGAGCC AAAGGTCTTG CAGA
              (MAMAGLOBIN)

SEQ ID NO. 5  GGCCAACAAA GCTCAGGACA ACA (PIP)

SEQ ID NO. 6  GCAGTGACTT CGTCATTTGG ACGTA (PIP)
```

Real-time PCR measurements were performed on an Applied Biosystems 7900 (Foster City Calif.). A thermal profile of 94 C for 2 min, followed by 50 cycles of 94 C for 15 sec, 62 C for 15 sec, and 72 C for 45 sec was used, as well as a threshold value of 275.

Results of these experiments are summarized in Table 1 and indicate no large differences in either RNA yield or amplification efficiency of the housekeeping gene, PBGD or the cancer genes mammaglobin and PIP between the samples extracted with shortened centrifugation steps as compared to the standard QIAGEN procedure. These results indicate that the rapid centrifugation protocol does not inhibit the reverse-transcription or PCR steps.

TABLE 1

Effect of Reduced Centrifugation Time on RNA yield and Real-time PCR in Breast lymph nodes.

| Sample | 260 | 280 | Ratio | ng/μl | Total Yield (μg) | Method of Extraction | Ct Values PBGD | MG | PIP |
|---|---|---|---|---|---|---|---|---|---|
| ALNC1.1 | 1.33 | 0.67 | 2.0 | 266 | 13.3 | Prior Art | 25.69 | 20.84 | 25.57 |
| ALNC1.2 | 1.11 | 0.57 | 1.9 | 222 | 11.1 | Prior Art | 23.77 | 19.19 | 24.76 |
| ALNC1.3 | 1.18 | 0.62 | 1.9 | 236 | 11.8 | Prior Art | 23.57 | 18.25 | 24.80 |
| ALNN2.1 | 0.97 | 0.482 | 2.0 | 195 | 9.7 | Prior Art | 26.24 | 23.37 | 26.63 |
| ALNN2.2 | 1.63 | 0.802 | 2.0 | 326 | 16.3 | Prior Art | 23.42 | 20.51 | 25.19 |
| ALNN2.3 | 1.61 | 0.799 | 2.0 | 322 | 16.1 | Prior Art | 26.01 | 22.14 | 24.84 |
| ALNC1.4 | 1.45 | 0.72 | 2.0 | 290 | 14.5 | 30 sec centrifugation | 25.60 | 18.49 | 24.10 |
| ALNC1.5 | 1.15 | 0.59 | 2.0 | 230 | 11.5 | 30 sec centrifugation | 25.44 | 20.07 | 25.80 |

TABLE 1-continued

Effect of Reduced Centrifugation Time on RNA yield and Real-time PCR in Breast lymph nodes.

| Sample | 260 | 280 | Ratio | Total Yield ng/µl | (µg) | Method of Extraction | Ct Values PBGD | MG | PIP |
|---|---|---|---|---|---|---|---|---|---|
| ALNC1.6 | 1.55 | 0.8 | 1.9 | 310 | 15.5 | 30 sec centrifugation | 24.35 | 19.36 | 25.92 |
| ALNN2.4 | 1.54 | 0.781 | 2.0 | 308 | 15.4 | 30 sec centrifugation | 25.15 | 23.96 | 27.02 |
| ALNN2.5 | 1.38 | 0.692 | 2.0 | 280 | 14.0 | 30 sec centrifugation | 23.90 | 20.57 | 25.46 |
| ALNN2.6 | 1.5 | 0.749 | 2.0 | 300 | 15.0 | 30 sec centrifugation | 23.60 | 20.35 | 25.98 |

As additional evidence for good RNA quality in the rapid protocol, RNA quality for all the above samples was also evaluated by means of an Agilent 2100Bioanalyzer using the 6000 Nano-chip Kit (Agilent Technologies, Wilmington Del.). Electropherogram results indicated comparable good quality RNA based on the presence of well-defined 18s and 28s ribosomal peaks with minimal RNA degradation. All samples had a ribosomal peak ratio near 1.6 or greater, based on the Agilent Bioanalyzer data, also confirming high quality RNA from the shortened centrifugation protocol. The total time for RNA extraction was 5 min 15 sec.

Example 2

RNA Yield, Reverse Transcription, and Real-Time PCR Amplification

In this experiment, a breast axillary node with ductal carcinoma was-used. All reagents were from the QIAGEN RNeasy Kit (cat 74181, QIAGEN, Inc. Valencia Corporation). The following supplies and equipment also were purchased from QIAGEN INC: QIAvac 24 filtering apparatus (cat 19403), QIAshredder (cat 79656), QIAvac connectors (cat 19409), and VacConnectors (cat 19407). All other reagents were obtained from sources as described in Example 1.

For this experiment tissue homogenization, 540 mg of breast node tissue was suspened in 10.8 ml of Buffer RLT and homogenized prior to use. The resultant homogenate was treated in several different ways.

Part I. Evaluation of Vacuum Manifold. This experiment was performed using a QIAvac 24 filtering apparatus with an applied vacuum.

1. 700 µL of homogenate were placed into a QIAshredder colum and centrifugated at 14,000 RPM for 2 min.
2. An equal volume of 70% ethanol was added to the lysate and mixed by pipetting. The next step was continued without delay
3. 700 µL of sample was applied to an, RNEasy mini column attached to a vacuum manifold. Vacuum was applied at 12 psi for 10 sec.
4. 700 µL of Buffer RWI were applied to the column, and the same vacuum pressure was applied for the same duration.
5. 500 µL of Buffer RPE were pipetted onto the column and the same vacuum pressure was applied for the same duration. Another 500 µL of Buffer RPE was added to the column and the same vacuum pressure applied for the same duration.
6. The column was placed into a collection tub and centrifuged at 14,000 rpm for 1 min to dry the column.
7. The column was transferred to a new 1.5 ml tube. Pipet 25 µL of RNAse-free water directly onto the membrane.
8. The membrane was centrifuged for 60 sec to elute.

Part II was performed to determine the effect of reducing the centifugation time to 30 sec as well as the use of a vacuum manifold 1. 700 µL of homogenate were placed into a QIAshredder colum and centrifuged at 14,000 RPM for 30 sec.
2. An equal volume of 70% ethanol was added to the lysate and mixed by pipetting. The next step was continued without delay
3. 700 µL of sample was applied to an RNEasy mini column attached to a vacuum manifold. Vacuum was applied at 12 psi for 10 sec.
4. 700 µL of Buffer RWI was applied to the column, and vacuum applied as above.
5. 500 µL of Buffer RPE were pipetted onto the column and vacuum applied as above. Another 500 µL of Buffer RPE were applied to the column and vacuum applied as above.
6. The column was placed into a collection tube and centrifuged at 14,000 rpm for 30 sec to dry the column.
7. The column was transferd to a new 1.5 ml tube. 25 µL of RNAse-free water was pipetted directly onto the membrane.
8. Centrifugation was conducted for 30 sec to elute.

Part III. Use of lower speed centrifuge.

In this experiment, a model 10MVSS centrifuge, purchased from VWR Scientific, West Chester, Pa. was used in steps 1, 6 and 7 of Part II above at 10,000 rpm.

Part IV. Eliminate Column Drying Step.

As a negative control, an experiment was included in which step 6 (Part II) was eliminated from the procedure described in Part II.

RNA yield in each of these parts, 260/280 nm ratio of the RNA (an estimate of RNA purity), and real-time PCR assays based on SYBR Green for the housekeeping gene PBGD with 3' and 5' primers are shown in Table 2 below. Procedures and reagents are as described in Example 1.

TABLE 2

RNA extraction from a breast node.

| GCLNC-7 Sample | Protocol Description | Total RNA Yield (μg) | RNA Ratio (260/280) | PBGD 3' Ct | PBGD 5' Ct | MG Ct |
|---|---|---|---|---|---|---|
| 1 | Kit Manufacturer's Protocol (control) | 31.82 | 2.1 | 27.43 | 28.35 | 23.26 |
| 2A | Centrifugation time reduced | 30.35 | 2.1 | 27.55 | 28.4 | 23.2 |
| 2B | Eliminated 1 RPE Wash | 28.11 | 2.1 | 27.35 | 28.27 | 23.09 |
| 2C | Used VWR mini-microfuge | 27.91 | 2.1 | 27.14 | 28.51 | 22.98 |
| 2D | Eliminated column drying step | 15.17 | 2.1 | 27.36 | 49.69 | 23.01 |
| 2-1 | Modifications 1-2C made (all) | 23.5 | 2.1 | 27.42 | 29.77 | 23.56 |
| BBC-2 positive control | N/A | N/A | N/A | 30.18 | 28.36 | 17.6 |
| NTC negative control | N/A | N/A | N/A | 49.03 | 50 | 41.71 |

Results of these experiments indicate that protocol which increase speed and lower instrument costs resulted in some loss of yield of RNA. However, the amount of RNA yielded by the modified protocol is well above that which is required for a reverse transcriptase reaction (2 to 2.5 μg). Real-time PCR results confirm that this rapid protocol results in RNA that can be transcribed and quantified by real-time PCR.

Example 3

Rapid v. Prior Art Protocols (Based on Real-Time PCR with Taqman Assays)

A total of 16 H&E positive nodes and 15 H&E negative breast node samples were purchased from Genomics Collaborative. Two 30 mg pieces of tissue were cut from each node.

Part I. One 30 mg piece of tissue was processed as follows: 600 ul of Buffer RLT was added and the tissue sample was homogenized manually for 20-40 sec by means of a disposable tissue grinder (cat 15704-126, VWR Scientific, West Chester, Pa.). The tube was centrifuged for 3 min at maximum speed in Eppendorf model 5415 C microcentrifuge. The supernatant fluid was transferred to a new tube, and 1 volume of 70% ethanol was added.

Sample (700 μL) was applied to an RNeasy mini column placed on the QIAvac 24 vacuum manifold and the vacuum was applied. Buffer RWI (700 μL) and allowed to filter through the column. Buffer RPE (500 μL) was pipetted onto the column and allowed to filter through. Another 500 μL of Buffer RPE was added to the column, and allowed to filter through. The RNeasy column was placed in a 2 ml collection tube and centrifuged in a microfuge at maximum speed for 1 min. The RNA was then eluted from the column, by transfering the RNeasy colum to a new 1.5 ml collection tube, adding 50 ul of RNAase-free water, and centrifuging for 1 min at 8000×g.

Part II. The second 30 mg piece of breast node tissue was processed by a rapid protocol as follows: (1)The tissue piece was added to 600 μL of Buffer RLT and homogenized manually for 20-40 sec by means of a disposable tissue grinder. (2) The homogenate was centrifuged through a QIAshredder column for 30 sec at maximum speed. (3) 1 volume of 70% ethanol was added to the lysate and mixed by pipetting. (4) The sample was then applied to an RNeasy mini column placed on the QIAvac 24 vacuum manifold and a vacuum was applied. (5) 700 ul of Buffer RWI was added to the column, and allowed to filter through the column. (6) 500 ul of Buffer RPE was added onto the column and allowed to filter through. (7) The column was transferred to a 2 ml collection tube, and centrifuged for 30 sec at 10,000 rpm. (8) 25 μL of RNAase-free water was added to the membrane and the column was centrifuged for 30 sec at 10,000 rpm to elute the RNA. All centrifugation steps in the rapid protocol were performed on a model 10MVSS VWR centrifuge.

Extracted RNA was reverse transcribed, and RNA and cDNA were quantified as described previously in Example 1.

For Taqman assays, Taqman Core Reagent Kit, Gene Amp 101×PCR Buffer 1, Amp Erase Uracil N-glycosidase, and AmpliTaq Gold DNA Polymerase were purchased from Applied Biosystems, Foster City, Calif. All other reagents were from commercial sources described in example 1. Glycerol was purchased from Sigma Chemical Co (St. Louis, Mo.) and Tween 20 from Eastman Organic Chemicals (Rochester, N.Y.)

Mammaglobin primers (SEQ ID NO. 3 and SEQ ID NO. 4) were synthesized by Invitrogen Corp.(Carlsbad, Calif.). and the mammaglobin Taqman probe (SEQ ID NO. 7) from Epoch Biosciences (San Diego, Calif.). PBGD primers (SEQ ID NO 8 and SEQ ID NO. 9) were synthesized by QIAGEN Operon (Alameda, Calif.), and the probe (SEQ ID NO. 23) by SYNTHEGEN, LLC (Houston, Tex.). B305D primers (SEQ ID NO. 11 and SEQ ID NO. 12) were synthesized at Invitrogen Corp and the probe (SEQ ID NO. 13) by Applied Biosystems, Inc. For all Taqman probes, carboxyfluorescein (FAM) and carboxytetramethylrhodamine TAMRA) were used as the dye and quencher pair.

SEQ ID NO. 3    CAAACGGATG AAACTCTGAG CAATGTTGA

SEQ ID NO. 4    TCTGTGAGCC AAAGG TCTTG CAGA

-continued

| SEQ ID NO. 7 | 6-FAM - TGTTTATGCA ATTAATATAT GACAGCAGTC TTTGTG- TAMRA |
| SEQ ID NO. 8 | CTGAGGCACC TGGAAGGAGG |
| SEQ ID NO. 9 | CATCTTCATG CTGGGCAGGG |
| SEQ ID NO. 23 | 6- FAM-CCTGAGGCAC CTGGAAGGAG GCTGCAG TGT- TAMRA |
| SEQ ID NO. 11. | TCTGATAAAG GCCGTACAAT G |
| SEQ ID NO. 12 | TCACGACTTG CTGTTTTTGC TC |
| SEQ ID NO. 13 | 6-FAM-ATCAAAAAACA AGCATGGCCTA CACC- TAMRA |

For the Taqman assays, a master mix was prepared by adding 10 µL of 10×PCR Buffer#1, 14 µL of 25 mM MgCl$_2$, 8 µL of 10 mM dNTP's, 1 µL of AmpErase UNG (1 U/µL), 16 µL of gycerol, 1 µL of 1% w/v Tween 20, 0.75 µL of AmpliTaq Gold (5 U/µL), 6 µL of each primer from a 5 µM stock, 0.4 µL of a 10 µM stock of probe, and water to a final volume of 96 µL. Master mix (48 µL) and 2 µL of cDNA from each node sample were added to each optical reaction microtiter plate well. After capping with optical caps, the plates were processed in an ABI Prism 7900 HT Sequence Detection System (Applied Biosystems, Inc., Foster City, Calif.). Commercial reagents including Taqman PCR Core Reagent Kit, Taqman DNA Template Reagents, and Taqman B-actin Dectection Reagents were purchased from Applied Biosystems (Foster City, Calif.) and the assay was performed according to the protocol recommended by the manufacturer. A threshold value of 0.02 was used for analysis with the mammaglobin assay, 0.03 for the B305D assay, 0.08 for the B-actin assay, and 0.1 for the PBGD assay. The average of triplicate determination by Taqman assays are shown in Tables 3 and 4.

A comparison of the real-time measurement of the housekeeping genes B-actin (SEQ ID NO. 19) and PBGD are shown in Table 3 in 15 H&E negative node samples as well as 16 H&E positive nodes and two control cDNA samples are shown in Table 3. Results of these experiments indicate good agreement between Ct values obtained with the rapid method of this invention and prior art protocol confirming that RNA extracted by the rapid RNA extraction protocol is capable of being reverse transcribed and PCR amplified to a similar extent as RNA extracted based on the prior art protocol.

Table 4 compares gene expression results based on Ct value for the breast cancer markers mammaglobin and B305D (isoform C, SEQ ID NO. 14) with the same breast node samples evaluated in Table 3. To determine whether a correlation can be made between H&E positive and H&E negative breast node samples based on real-time PCR results, the lowest Ct value for each marker in the H&E negative node samples was identified for both mammaglobin and B305D. An arbitrary, but conservative, cut-off of 2.5Ct values less than this lowest value among H&E negative samples was applied to the H&E positive samples. Samples that are shaded in the Table 4 have higher expression for these two breast markers, in that Ct value is at least 2.5Ct values lower than a Ct value observed among H&E negative samples. There was a good correlation in expression of these markers using both the rapid method of this invention and the prior art method as recommended by the manufacturer of the kit, QIAGEN.

Using mammaglobin as a marker in one of 15 H&E negative nodes samples, GCLNC-24 exhibited difference in Ct value of 0.4 which is within experimental error. The second sample showed a larger difference in Ct. larger differences in Ct value with both mammaglobin and B305D may be due to difficulties in spectrally quantifying RNA in these samples as well as to possible sampling problems due to the well established non-uniform distribution of metastases in nodes. (Cserni. 1999. Metastases in axillary sentinel lymph nodes in breast cancer as detected by intensive histopathological work up. J. Clin Pathol, 52:0922-924).

TABLE 3

Comparison of RNA extracted by the rapid method and Prior Art Method as measured by Taqman Assays for the Housekeeping Genes B-actin and PBGD

|  |  |  | B-Actin Ct Values | | PBGD Ct Values | |
| --- | --- | --- | --- | --- | --- | --- |
|  | Sample | Template | Qiagen | Rapid | Qiagen | Rapid |
| H&E Negative | 1 | GCLNN-10 | 20.7 | 21.9 | 32.6 | 34.1 |
|  | 2 | GCLNN-11 | 20.5 | 21.0 | 33.7 | 32.7 |
|  | 3 | GCLNN-12 | 21.7 | 22.5 | 32.8 | 32.8 |
|  | 4 | GCLNN-14 | 21.2 | 19.1 | 32.1 | 31.0 |
|  | 5 | GCLNN-15 | 19.8 | 21.3 | 32.5 | 39.9 |
|  | 6 | GCLNN-19 | 22.4 | 23.0 | 29.9 | 39.1 |
|  | 7 | GCLNN-20 | 17.8 | 18.6 | 31.7 | 30.9 |
|  | 8 | GCLNN-23 | 21.4 | 19.2 | 33.1 | 31.4 |
|  | 9 | GCLNN-24 | 21.1 | 26.1 | 36.9 | 37.0 |
|  | 10 | GCLNN-25 | 19.1 | 21.4 | 32.7 | 33.1 |
|  | 11 | GCLNN-26 | 23.8 | 26.7 | 40.0 | 39.7 |
|  | 12 | CBLNN-274 | 20.1 | 19.8 | 31.5 | 30.7 |
|  | 13 | CBLNN-257 | 20.4 | 22.6 | 32.8 | 34.0 |
|  | 14 | CBLNN-258 | 23.4 | 27.6 | 33.1 | 35.4 |
|  | 15 | CBLNN-262 | 23.0 | 23.6 | 33.0 | 32.1 |
| H&E Positive | 16 | GCLNC-1 | 18.7 | 18.5 | 28.8 | 29.1 |
|  | 17 | GCLNC-5 | 20.4 | 21.6 | 31.3 | 31.0 |
|  | 18 | GCLNC-6 | 20.0 | 19.9 | 31.4 | 30.2 |
|  | 19 | GCLNC-7 | 20.6 | 28.2 | 29.3 | 32.1 |
|  | 20 | GCLNC-11 | 18.9 | 19.5 | 31.2 | 30.9 |
|  | 21 | GCLNC-12 | 26.1 | 23.8 | 32.6 | 31.2 |
|  | 22 | GCLNC-13 | 20.5 | 18.9 | 30.8 | 27.7 |
|  | 23 | GCLNC-16 | 20.5 | 22.7 | 31.1 | 30.5 |
|  | 24 | GCLNC-17 | 22.1 | 19.4 | 40.0 | 29.1 |
|  | 25 | GCLNC-20 | 20.0 | 19.5 | 31.9 | 29.6 |
|  | 26 | GCLNC-21 | 21.1 | 21.3 | 33.5 | 32.2 |
|  | 27 | GCLNC-22 | 24.2 | 22.9 | 29.3 | 32.1 |
|  | 28 | GCLNC-23 | 18.4 | 20.7 | 29.6 | 35.5 |
|  | 29 | GCLNC-24 | 19.1 | 19.5 | 29.4 | 30.1 |
|  | 31 | ALNC-1 | 21.1 | 19.4 | 30.2 | 30.8 |
|  | 32 | ALNN-2 | 18.9 | 19.5 | 31.4 | 30.0 |
|  | 33 | CBLNN-247 | 18.2 | 20.7 | 31.5 | 31.1 |

TABLE 4

Comparison of RNA extracted by the rapid method and by the Prior Art Method as measured by Taqman Assays for the Cancer Genes Mammaglobin and B305D

|  |  |  | MG Ct Values | | B305D-A/C Ct Values | |
|---|---|---|---|---|---|---|
|  | Sample | Template | Qiagen | Rapid | Qiagen | Rapid |
| H & E Negative | 1 | GCLNN-10 | 40.0 | 40.0 | 40.0 | 40.0 |
|  | 2 | GCLNN-11 | 40.0 | 40.0 | 40.0 | 40.0 |
|  | 3 | GCLNN-12 | 40.0 | 40.0 | 39.7 | 39.9 |
|  | 4 | GCLNN-14 | 40.0 | 40.0 | 39.6 | 39.9 |
|  | 5 | GCLNN-15 | 40.0 | 40.0 | 39.6 | 40.0 |
|  | 6 | GCLNN-19 | 40.0 | 40.0 | 40.0 | 40.0 |
|  | 7 | GCLNN-20 | 40.0 | 40.0 | 38.6 | 38.6 |
|  | 8 | GCLNN-23 | 40.0 | 40.0 | 39.0 | 40.0 |
|  | 9 | GCLNN-24 | 40.0 | 40.0 | 40.0 | 40.0 |
|  | 10 | GCLNN-25 | 40.0 | 40.0 | 40.0 | 40.0 |
|  | 11 | GCLNN-26 | 36.2 | 40.0 | 40.0 | 40.0 |
|  | 12 | CBLNN-274 | 40.0 | 40.0 | 39.3 | 39.5 |
|  | 13 | CBLNN-257 | 40.0 | 40.0 | 40.0 | 39.5 |
|  | 14 | CBLNN-258 | 40.0 | 40.0 | 40.0 | 40.0 |
|  | 15 | CBLNN-262 | 40.0 | 40.0 | 39.6 | 39.5 |
| H & E Positive | 16 | GCLNC-1 | 20.8 | 22.8 | 27.1 | 27.9 |
|  | 17 | GCLNC-5 | 39.7 | 40.0 | 29.2 | 36.6 |
|  | 18 | GCLNC-6 | 23.7 | 22.7 | 26.8 | 26.3 |
|  | 19 | GCLNC-7 | 27.9 | 28.3 | 30.0 | 31.0 |
|  | 20 | GCLNC-11 | 32.5 | 32.8 | 28.2 | 28.4 |
|  | 21 | GCLNC-12 | 32.4 | 30.7 | 38.6 | 36.4 |
|  | 22 | GCLNC-13 | 40.0 | 39.7 | 38.9 | 38.3 |
|  | 23 | GCLNC-16 | 20.8 | 21.7 | 36.5 | 35.9 |
|  | 24 | GCLNC-17 | 30.7 | 28.7 | 32.3 | 24.9 |
|  | 25 | GCLNC-20 | 30.6 | 30.1 | 26.8 | 27.8 |
|  | 26 | GCLNC-21 | 40.0 | 38.9 | 34.0 | 35.2 |
|  | 27 | GCLNC-22 | 39.4 | 36.3 | 36.4 | 31.4 |
|  | 28 | GCLNC-23 | 33.0 | 33.8 | 30.1 | 30.8 |
|  | 29 | GCLNC-24 | 37.6 | 37.2 | 28.0 | 29.7 |
|  | 31 | ALNC-1 | 23.8 | 24.8 | 25.6 | 28.6 |
|  | 32 | ALNN-2 | 27.7 | 27.6 | 23.4 | 23.9 |
|  | 33 | CBLNN-247 | 35.9 | 38.2 | 29.8 | 30.1 |
| Cut Off Values = | | | 33.7 | 37.5 | 36.1 | 36.1 |

Example 4

Evaluation of a QIAshredder Column

It is the purpose of this example to demonstrate that the QIAshredder column can be used after homogenization of lymph node tissue, and that centrifugation of the homogenate for only 30 seconds yields acceptable RNA extraction.

A breast axillary node that was H&E—negative was obtained from Genomics Collaborative (Cambridge, Mass.). A 490 mg slice of tissue was mixed with 5.5 ml of Buffer RLT, and the node was homogenized. Six hundred microliters of homogenate was removed and RNA was extracted using all the protocol shortening modifications as described in Example 2. As a control, another 600 µL of homogenate was treated using all the protocol shortening modifications as described in Example 2, except that a 3 min centrifugation was used instead of the QIAshredder column. The RNA from each reaction was reverse transcribed and quantified as described in Example 1. Real-time PCR was performed using Taqman probes as described previously in Example 3.

Results of these studies indicated similar RNA yields of 0.31 µg/µL in the protocol involving the QIAshredder protocol as compared to 0.34 µg/µL in the centrifugation protocol. Identical 260/280 nm ratio's of 2.1 were obtained in both samples indicating high quality RNA. Real-time PCR assays also indicated similar Ct values for Mammaglobin with RNA extracted by the QIAshredder column as compared to the protocol involving (22.5 versus 22.0), as well as with B305D (26.7 versus 26.6) as well as with the housekeeping genes PBGD (29.1 versus 29.0), and B-actin (18.5 versus 18.2).

In summary, this experiment indicates similar RNA yield, quality and real-time PCR amplfication results with the protocol involving a QIAshredder substituted for a 3 min centrifugation step after homogenization. This modification reduces the time required to perform RNA extraction by 2.5 minutes, which is important in developing protocols suitable for intraoperative and other applications in which fast results are required to impact patient care.

Example 5

Comparison of Rapid RNA Extraction Method and Standard (Prior Art) QIAGEN Protocol on Colon Tissue The following example compares the extraction of RNA from colon tissue with both the method of the invention and the prior art. Twenty mg of colon tissue was added to 600 ul of Buffer RLT and homogenized as described in Example 3. One sample of homogenizaed colon cancer tissue was treated according to the rapid procol as described in Example 3A and one sample was treated according to the QIAGEN protocol as described in Example 3, part B. Resultant RNA from both procedures was tested on the Agilent Bioanalyzer.

Electropherograms for RNA extracted with the rapid method and the prior art showed that the RNA ratio of sample processed with the QIAGEN protocol was 1.54 and the sample treated with the rapid protocol was 1.37. Generally, any sample with an RNA ratio above 1.1 is considered acceptable. As determined by the Agilent Bioanalyzer, the sample processed with rapid protocol had an RNA yield of 136 ug/ml, whereas the sample treated with the QIAGEN method had a yield of 280 ug/ml. The yield obtained by both protocol is well above that which is required for a reverse transcriptase reaction (2 to 2.5 ug).

Example 6

Effect of Diluting of Lysate on RNA Yield and Precision

The following example illustrates the effect of dilution of the lysate on RNA yield and precision of RNA recovery. In this example. 20 mg. 10 mg or 5 mg of frozen pig node tissue was cut. Tissue was ground using a 50 ml Disposable Tissue Grinder for 30 sec, and the samples were vortexed. Three replicates were performed for each node weight. One ml of each lysate was transferred to a 1.7 ml microceatrifuge tube which was then centrifuged in an Eppendorf microfuge at maximum speed (14,000 RPM) for 30 sec. Seven hundred microliters was centrifuged through a QIAshredder column and the samples were centrifuged at maximum speed for 30 sec. The column was then washed, the column dried, and RNA eluted as described previously in Example 2, Part 1 steps 4-8. RNA was quantified by means of a Gene Spec II. Results of these studies are shown in FIG. 1, and illustrates excellent precision at an initial node tissue weight of 2.5 mg homogenized in 600 ml of homogenization buffer, as compared to samples with higher weights including 10 mg and 20 mg node tissue. These results indicate that improved precision of RNA recovery can be obtained at lower node weight. Also, it would be expected that more dilute homogenates would be filtered faster through the column, and that there would be even fewer potential problems with filter clogging.

Example 7

The following example was performed to demonstrate that with dilution of the homogenate, there is no need for a centrifugation step after homogenization, and that processing through a device such as a QIAshredder is not necessary to rapidly extract RNA.

In this example, each 200 mg piece of pig lymph node tissue was suspended in 4 ml of homogenization Buffer RLT and homogenized in a disposable 50 ml Tissue Grinder for 30 sec. An additional 20 ml of Buffer RLT was added so that the final concentration of tissue was 5 mg in 600 ml of buffer. The sample was vortexed for 15 sec and the tissue concentration was diluted to either 2.5 mg, 1.25 mg, or 0.625 mg in 600 ml of Buffer RLT. Triplicate determinations for the following variables were performed: (I) centrifugation after homogenization and QIAshredder step, (II) centrifugation, no QIAshredder step, (III) QIAshredder, no centrifugation step, and (IV), no QIAshredder, no centrifugation of the homogenate after tissue homogenization. Each sample was diluted with an equal volume of 70% ethanol, and mixed. The sample (700 ul) was applied to a RNEasay mini column, and placed on a QIAGEN vacuum manifold. The sample was filtered by vacuum, and the column washed with 700 ul of Buffer RWI Buffer, followed by 500 ul of Buffer RPE. The column was added to a new collection tube and centrifuged at full speed (14,000 RPM) for 30 sec to dry the column. Each column then was transferred to a new collection tube, and 50 ul of RNAase-free water was pipetted onto the membrane, and the tube was centrifuged for 30 sec at 14,000×g to elute the RNA. RNA yield was quantified spectropbotometrically. Results of these studies are shown in FIG. 2, and indicate that at the samples with lower weight of tissue (2.5 mg, 1.25 mg, and 0.625 mg), no improvement is seen when either the QIAshredder, or a centrifugation step after homogenization, or both are included in the assay.

We claim:

1. A method of extracting RNA from biological systems consisting of adding a sample solution comprising homogenized tissue or blood to a substrate containing or to which is affixed a material binding to RNA, centrifuging said substrate or material for no more than 30 seconds, adding one wash buffer to said substrate or material, allowing said wash buffer to filter through said substrate or material, adding another wash buffer to said substrate or material and centrifuging for no more than 30 seconds or applying negative pressure to said substrate or material, transferring said substrate or material to a collection tube, adding water to said substrate or material in said collection tube, centrifuging said substrate or material for no more than 30 seconds, and withdrawing RNA from said collection tube wherein said method of extracting RNA is conducted in no more than 3 minutes.

2. The method of claim 1 wherein the tissue is homogenized by means of a tissue grinder.

3. The method of claim 1 wherein negative pressure is applied from 11.6 to 13.1 psi.

* * * * *

SEQUENCE LISTING

<160> NUMBER OF SEQ ID NOS: 35

<210> SEQ ID NO 1
<211> LENGTH: 27
<212> TYPE: DNA
<213> ORGANISM: Artificial
<220> FEATURE:
<223> OTHER INFORMATION: Artificial Sequence is a Primer

<400> SEQUENCE: 1
tcccatcaga atccaaacaa gaggaag                                        27

<210> SEQ ID NO 2
<211> LENGTH: 26
<212> TYPE: DNA
<213> ORGANISM: Artificial
<220> FEATURE:
<223> OTHER INFORMATION: artifiical sequence is a primer

<400> SEQUENCE: 2
ggctgttgct tggacttctc taaaga                                         26

<210> SEQ ID NO 3
<211> LENGTH: 29
<212> TYPE: DNA
<213> ORGANISM: Artificial
<220> FEATURE:
<223> OTHER INFORMATION: Artificial sequence is a primer

<400> SEQUENCE: 3
caaacggatg aaactctgag caatgttga                                      29

<210> SEQ ID NO 4
<211> LENGTH: 24
<212> TYPE: DNA
<213> ORGANISM: Artificial
<220> FEATURE:
<223> OTHER INFORMATION: Artficial sequence is a primer

<400> SEQUENCE: 4
tctgtgagcc aaaggtcttg caga                                           24

```
<210> SEQ ID NO 5
<211> LENGTH: 23
<212> TYPE: DNA
<213> ORGANISM: Artificial
<220> FEATURE:
<223> OTHER INFORMATION: Artificial sequence is a  primer

<400> SEQUENCE: 5
ggccaacaaa gctcaggaca aca                                             23

<210> SEQ ID NO 6
<211> LENGTH: 25
<212> TYPE: DNA
<213> ORGANISM: Artificial
<220> FEATURE:
<223> OTHER INFORMATION: Artificial sequence is a Primer

<400> SEQUENCE: 6
gcagtgactt cgtcatttgg acgta                                           25

<210> SEQ ID NO 7
<211> LENGTH: 36
<212> TYPE: DNA
<213> ORGANISM: Artificial
<220> FEATURE:
<223> OTHER INFORMATION: Artificial sequence is a Probe

<400> SEQUENCE: 7
tgtttatgca attaatatat gacagcagtc tttgtg                               36

<210> SEQ ID NO 8
<211> LENGTH: 20
<212> TYPE: DNA
<213> ORGANISM: Artificial
<220> FEATURE:
<223> OTHER INFORMATION: Artificial sequence is a Primer

<400> SEQUENCE: 8
ctgaggcacc tggaaggagg                                                 20

<210> SEQ ID NO 9
<211> LENGTH: 20
<212> TYPE: DNA
<213> ORGANISM: Artificial
<220> FEATURE:
<223> OTHER INFORMATION: Artificial sequence is a Primer

<400> SEQUENCE: 9
catcttcatg ctgggcaggg                                                 20

<210> SEQ ID NO 10
<211> LENGTH: 29
<212> TYPE: DNA
<213> ORGANISM: Artificial
<220> FEATURE:
<223> OTHER INFORMATION: Artificial sequence is a Primer

<400> SEQUENCE: 10
ctgaggcacc tggaaggagg ctgcagtgt                                       29

<210> SEQ ID NO 11
<211> LENGTH: 21
<212> TYPE: DNA
<213> ORGANISM: Artificial
<220> FEATURE:
<223> OTHER INFORMATION: Artificial sequence is a Primer
```

```
<400> SEQUENCE: 11
tctgataaag gccgtacaat g                                              21

<210> SEQ ID NO 12
<211> LENGTH: 22
<212> TYPE: DNA
<213> ORGANISM: Artificial
<220> FEATURE:
<223> OTHER INFORMATION: Artificial sequence is a Primer

<400> SEQUENCE: 12
tcacgacttg ctgtttttgc tc                                             22

<210> SEQ ID NO 13
<211> LENGTH: 26
<212> TYPE: DNA
<213> ORGANISM: Artificial
<220> FEATURE:
<223> OTHER INFORMATION: Artificial sequence is a Probe

<400> SEQUENCE: 13
atcaaaaaac aagcatggcc tacacc                                         26

<210> SEQ ID NO 14
<211> LENGTH: 1155
<212> TYPE: DNA
<213> ORGANISM: Human

<400> SEQUENCE: 14
atggtggttg aggttgattc catgccggct gcctcttctg tgaagaagcc atttggtctc      60
aggagcaaga tgggcaagtg gtgctgccgt tgcttcccct gctgcaggga gagcggcaag     120
agcaacgtgg gcacttctgg agaccacgac gactctgcta tgaagacact caggagcaag     180
atgggcaagt ggtgccgcca ctgcttcccc tgctgcaggg ggagtggcaa gagcaacgtg     240
ggcgcttctg gagaccacga cgactctgct atgaagacac tcaggaacaa gatgggcaag     300
tggtgctgcc actgcttccc ctgctgcagg gggagcagca gagcaaggt gggcgcttgg      360 ggagactacg atgacagtgc cttcatggag cccaggtacc acgtccgtgg agaagatctg     420
gacaagctcc acagagctgc ctggtggggt aaagtcccca gaaaggatct catcgtcatg     480
ctcagggaca ctgacgtgaa caagcaggac aagcaaaaga ggactgctct acatctggcc     540
tctgccaatg ggaattcaga agtagtaaaa ctcctgctgg acagacgatg tcaacttaat     600
gtccttgaca caaaaagag gacagctctg ataaaggccg tacaatgcca ggaagatgaa     660
tgtgcgttaa tgttgctgga acatggcact gatccaaata ttccagatga gtatggaaat     720
accactctgc actacgctat ctataatgaa gataaattaa tggccaaagc actgctctta     780
tatggtgctg atatcgaatc aaaaaacaag catggcctca caccactgtt acttggtgta     840
catgagcaaa acagcaagt cgtgaaattt ttaattaaga aaaagcgaa tttaaatgca      900 ctggatagat atggaaggac tgctctcata cttgctgtat gttgtggatc agcaagtata     960
gtcagccttc tacttgagca aaatattgat gtatcttctc aagatctatc tggacagacg    1020
gccagagagt atgctgtttc tagtcatcat catgtaattt gccagttact ttctgactac    1080
aaagaaaaac agatgctaaa aatctcttct gaaaacagca atccagaaaa tgtctcaaga    1140
accagaaata aataa                                                   1155

<210> SEQ ID NO 15
```

-continued

<211> LENGTH: 3865
<212> TYPE: DNA
<213> ORGANISM: Human

<400> SEQUENCE: 15

| | | | | | |
|---|---|---|---|---|---|
| tccgagctga | ttacagacac | caaggaagat | gctgtaaaga | gtcagcagcc | acagccctgg | 60 |
| ctagctggcc | ctgtgggcat | ttattagtaa | agtttttaatg | acaaaagctt | tgagtcaaca | 120 |
| cacccgtggg | taattaacct | ggtcatcccc | accctggaga | gccatcctgc | ccatgggtga | 180 |
| tcaaagaagg | aacatctgca | ggaacacctg | atgaggctgc | acccttggcg | aaagaacac | 240 |
| ctgacacagc | tgaaagcttg | gtggaaaaaa | cacctgatga | ggctgcaccc | ttggtggaaa | 300 |
| gaacacctga | cacggctgaa | agcttggtgg | aaaaaacacc | tgatgaggct | gcatccttgg | 360 |
| tggagggaac | atctgacaaa | attcaatgtt | tggagaaagc | gacatctgga | aagttcgaac | 420 |
| agtcagcaga | agaaacacct | agggaaatta | cgagtcctgc | aaaagaaaca | tctgagaaat | 480 |
| ttacgtggcc | agcaaaagga | agacctagga | agatcgcatg | ggagaaaaaa | gaagacacac | 540 |
| ctagggaaat | tatgagtccc | gcaaaagaaa | catctgagaa | atttacgtgg | gcagcaaaag | 600 |
| gaagacctag | gaagatcgca | tgggagaaaa | aagaaacacc | tgtaaagact | ggatgcgtgg | 660 |
| caagagtaac | atctaataaa | actaaagttt | tggaaaaagg | aagatctaag | atgattgcat | 720 |
| gtcctacaaa | agaatcatct | acaaaagcaa | gtgccaatga | tcagaggttc | ccatcagaat | 780 |
| ccaaacaaga | ggaagatgaa | gaatattctt | gtgattctcg | gagtctcttt | gagagttctg | 840 |
| caaagattca | agtgtgtata | cctgagtcta | tatcaaaaa | agtaatggag | ataaatagag | 900 |
| aagtagaaga | gcctcctaag | aagccatctg | ccttcaagcc | tgccattgaa | atgcaaaact | 960 |
| ctgttccaaa | taaagccttt | gaattgaaga | atgaacaaac | attgagagca | gatccgatgt | 1020 |
| tcccaccaga | atccaaacaa | aaggactatg | aagaaaattc | ttgggattct | gagagtctct | 1080 |
| gtgagactgt | ttcacagaag | gatgtgtgtt | tacccaaggc | tacacatcaa | aaagaaatag | 1140 |
| ataaaataaa | tggaaaatta | gaagagtctc | ctaataaaga | tggtcttctg | aaggctacct | 1200 |
| gcggaatgaa | agtttctatt | ccaactaaag | ccttagaatt | gaaggacatg | caaactttca | 1260 |
| aagcagagcc | tccggggaag | ccatctgcct | tcgagcctgc | cactgaaatg | caaaagtctg | 1320 |
| tcccaaataa | agccttggaa | ttgaaaaatg | aacaaacatt | gagagcagat | gagatactcc | 1380 |
| catcagaatc | caaacaaaag | gactatgaag | aaagttcttg | ggattctgag | agtctctgtg | 1440 |
| agactgtttc | acagaaggat | gtgtgtttac | ccaaggctrc | rcatcaaaaa | gaaatagata | 1500 |
| aaataaatgg | aaaattagaa | gggtctcctg | ttaaagatgt | tcttctgaag | gctaactgcg | 1560 |
| gaatgaaagt | ttctattcca | actaaagcct | tagaattgat | ggacatgcaa | actttcaaag | 1620 |
| cagagcctcc | cgagaagcca | tctgccttcg | agcctgccat | tgaaatgcaa | aagtctgttc | 1680 |
| caaataaagc | cttggaattg | aagaatgaac | aaacattgag | agcagatgag | atactcccat | 1740 |
| cagaatccaa | acaaaaggac | tatgaagaaa | gttcttggga | ttctgagagt | ctctgtgaga | 1800 |
| ctgtttcaca | gaaggatgtg | tgtttaccca | aggctrcrca | tcaaaaagaa | atagataaaa | 1860 |
| taaatggaaa | attagaagag | tctcctgata | atgatggttt | tctgaaggct | ccctgcagaa | 1920 |
| tgaaagtttc | tattccaact | aaagccttag | aattgatgga | catgcaaact | ttcaaagcag | 1980 |
| agcctcccga | gaagccatct | gccttcgagc | ctgccattga | aatgcaaaag | tctgttccaa | 2040 |
| ataaagcctt | ggaattgaag | aatgaacaaa | cattgagagc | agatcagatg | ttcccttcag | 2100 |
| aatcaaaaca | aaagaasgtt | gaagaaaatt | cttgggattc | tgagagtctc | cgtgagactg | 2160 |
| tttcacagaa | ggatgtgtgt | gtacccaagg | ctacacatca | aaaagaaatg | gataaaataa | 2220 |

-continued

```
gtggaaaatt agaagattca actagcctat caaaaatctt ggatacagtt cattcttgtg    2280
aaagagcaag ggaacttcaa aaagatcact gtgaacaacg tacaggaaaa atggaacaaa    2340
tgaaaaagaa gttttgtgta ctgaaaaaga aactgtcaga agcaaagaa ataaaatcac     2400 agttagagaa ccaaaaagtt aaatgggaac aagagctctg cagtgtgaga ttgactttaa    2460
accaagaaga agaaagaga agaaatgccg atatattaaa tgaaaaaatt agggaagaat     2520
taggaagaat cgaagagcag cataggaaag agttagaagt gaaacaacaa cttgaacagg    2580
ctctcagaat acaagatata gaattgaaga gtgtagaaag taatttgaat caggtttctc    2640
acactcatga aaatgaaaat tatctcttac atgaaaattg catgttgaaa aggaaattg     2700 ccatgctaaa actggaaata gccacactga acaccaata ccaggaaaag gaaaataaat     2760
actttgagga cattaagatt ttaaaagaaa agaatgctga acttcagatg accctaaaac    2820
tgaaagagga atcattaact aaaagggcat ctcaatatag tgggcagctt aaagttctga    2880
tagctgagaa cacaatgctc acttctaaat tgaaggaaaa acaagacaaa gaaatactag    2940
aggcagaaat tgaatcacac catcctagac tggcttctgc tgtacaagac catgatcaaa    3000
ttgtgacatc aagaaaaagt caagaacctg cttccacat tgcaggagat gcttgtttgc     3060
aaagaaaaat gaatgttgat gtgagtagta cgatatataa caatgaggtg ctccatcaac    3120
cactttctga agctcaaagg aaatccaaaa gcctaaaaat taatctcaat tatgcmggag    3180
atgctctaag agaaaataca ttggtttcag aacatgcaca agagaccaa cgtgaaacac     3240 agtgtcaaat gaaggaagct gaacacatgt atcaaaacga acaagataat gtgaacaaac    3300
acactgaaca gcaggagtct ctagatcaga aattatttca actacaaagc aaaaatatgt    3360
ggcttcaaca gcaattagtt catgcacata gaaagctga caacaaaagc aagataacaa     3420
ttgatattca ttttcttgag aggaaaatgc aacatcatct cctaaaagag aaaaatgagg    3480
agatatttaa ttacaataac catttaaaaa accgtatata tcaatatgaa aaagagaaag    3540
cagaaacaga aaactcatga gagacaagca gtaagaaact tcttttggag aaacaacaga    3600
ccagatcttt actcacaact catgctagga ggccagtcct agcatcacct tatgttgaaa    3660
atcttaccaa tagtctgtgt caacagaata cttattttag aagaaaaatt catgatttct    3720
tcctgaagcc tacagacata aaataacagt gtgaagaatt acttgttcac gaattgcata    3780
aagctgcaca ggattcccat ctaccctgat gatgcagcag acatcattca atccaaccag    3840
aatctcgctc tgtcactcag gctgg                                          3865
```

<210> SEQ ID NO 16
<211> LENGTH: 3282
<212> TYPE: DNA
<213> ORGANISM: Human

<400> SEQUENCE: 16

```
gggacagggc tgaggatgag gagaaccctg gggacccaga agaccgtgcc ttgcccggaa      60
gtcctgcctg taggcctgaa ggacttgccc taacagagcc tcaacaacta cctggtgatt     120
cctacttcag ccccttggtg tgagcagctt ctcaacatga actacagcct ccacttggcc     180
ttcgtgtgtc tgagtctctt cactgagagg atgtgcatcc aggggagtca gttcaacgtc     240
gaggtcggca gaagtgacaa gctttccctg cctggctttg agaacctcac agcaggatat    300
aacaaatttc tcaggcccaa ttttggtgga gaacccgtac agatagcgct gactctggac    360
attgcaagta tctctagcat ttcagagagt aacatggact acacagccac catataccctc   420
```

```
cgacagcgct ggatggacca gcggctggtg tttgaaggca acaagagctt cactctggat    480
gcccgcctcg tggagttcct ctgggtgcca gatacttaca ttgtggagtc caagaagtcc    540
ttcctccatg aagtcactgt gggaaacagg ctcatccgcc tcttctccaa tggcacggtc    600
ctgtatgccc tcagaatcac gacaactgtt gcatgtaaca tggatctgtc taaatacccc    660
atggacacac agacatgcaa gttgcagctg gaaagctggg gctatgatgg aaatgatgtg    720
gagttcacct ggctgagagg gaacgactct gtgcgtggac tggaacacct gcggcttgct    780
cagtacacca tagagcggta tttcaccttg gtcaccagat cgcagcagga gacaggaaat    840
tacactagat tggtcttaca gtttgagctt cggaggaatg ttctgtattt cattttggaa    900
acctacgttc cttccacttt cctggtggtg ttgtcctggg tttcattttg gatctctctc    960
gattcagtcc ctgcaagaac ctgcattgga gtgacgaccg tgttatcaat gaccacactg   1020
atgatcgggt cccgcacttc tcttcccaac accaactgct tcatcaaggc catcgatgtg   1080
tacctgggga tctgctttag cttttgtgttt ggggccttgc tagaatatgc agttgctcac   1140
tacagttcct tacagcagat ggcagccaaa gataggggga caacaaagga agtagaagaa   1200
gtcagtatta ctaatatcat caacagctcc atctccagct ttaaacggaa gatcagcttt   1260
gccagcattg aaatttccag cgacaacgtt gactacagtg acttgacaat gaaaaccagc   1320
gacaagttca gtttgtcttc cgagaaaag atgggcagga ttgttgatta tttcacaatt   1380 caaaaccca gtaatgttga tcactattcc aaactactgt ttcctttgat ttttatgcta   1440
gccaatgtat tttactgggc atactacatg tattttttgag tcaatgttaa atttcttgca   1500
tgccataggt cttcaacagg acaagataat gatgtaaatg gtattttagg ccaagtgtgc   1560
acccacatcc aatggtgcta caagtgactg aaataatatt tgagtctttc tgctcaaaga   1620
atgaagctcc aaccattgtt ctaagctgtg tagaagtcct agcattatag gatcttgtaa   1680
tagaaacatc agtccattcc tctttcatct taatcaagga cattcccatg gagcccaaga   1740
ttacaaatgt actcagggct gtttattcgg tggctccctg gtttgcattt acctcatata   1800
aagaatggga aggagaccat tgggtaaccc tcagtgtgtca gaagttgttt ctaaagtaac   1860
tatacatgtt ttttactaaa tctctgcagt gcttataaaa tacattgttg cctatttagg   1920
gagtaacatt ttctagtttt tgtttctggt taaaatgaaa tatgggctta tgtcaattca   1980
ttggaagtca atgcactaac tcaataccaa gatgagtttt taaataatga atattattta   2040
ataccacaac agaattatcc ccaatttcca ataagtccta tcattgaaaa ttcaaatata   2100
agtgaagaaa aaattagtag atcaacaatc taaacaaatc cctcggttct aagatacaat   2160
ggattcccca tactgaaagg actctgaggc tttattcccc cactatgcat atcttatcat   2220
tttattatta tacacacatc catcctaaac tatactaaag ccctttttccc atgcatggat   2280 ggaaatggaa gattttttg taacttgttc tagaagtctt aatatgggct gttgccatga   2340
aggcttgcag aattgagtcc attttctagc tgcctttatt cacatagtga tggggtacta   2400
aaagtactgg gttgactcag agagtcgctg tcattctgtc attgctgcta ctctaacact   2460
gagcaacact ctcccagtgg cagatcccct gtatcattcc aagaggagca ttcatccctt   2520
tgctctaatg atcaggaatg atgcttatta gaaacaaac tgcttgaccc aggaacaagt   2580
ggcttagctt aagtaaactt ggctttgctc agatccctga tccttccagc tggtctgctc   2640
tgagtggctt atcccgcatg agcaggagcg tgctggccct gagtactgaa ctttctgagt   2700
aacaatgaga cacgttacag aacctatgtt caggttgcgg gtgagctgcc ctctccaaat   2760
ccagccagag atgcacattc ctcggccagt ctcagccaac agtaccaaaa gtgattttg   2820
```

```
agtgtgccag ggtaaaggct tccagttcag cctcagttat tttagacaat ctcgccatct    2880
ttaatttctt agcttcctgt tctaataaat gcacggcttt acctttcctg tcagaaataa    2940
accaaggctc taaagatgag tttcccttct gtaactccct agagccacag gttctcattc    3000
cttttcccat tatacttctc acaattcagt ttctatgagt ttgatcacct gattttttta    3060
acaaaatatt tctaacggga atgggtggga gtgctggtga aaagagatga aatgtggttg    3120
tatgagccaa tcatatttgt gatttttttaa aaaagtttta aaggaaata tctgttctga     3180 aaccccactt aagcattgtt tttatataaa acaatgata aagatgtgaa ctgtgaaata      3240
aatataccat attagctacc caccaaaaaa aaaaaaaaaa aa                        3282

<210> SEQ ID NO 17
<211> LENGTH: 503
<212> TYPE: DNA
<213> ORGANISM: Human

<400> SEQUENCE: 17
gacagcggct tccttgatcc ttgccacccg cgactgaaca ccgacagcag cagcctcacc      60
atgaagttgc tgatggtcct catgctggcg gccctctccc agcactgcta cgcaggctct     120
ggctgcccct tattggagaa tgtgatttcc aagacaatca atccacaagt gtctaagact     180
gaatacaaag aacttcttca agagttcata gacgacaatg ccactacaaa tgccatagat     240
gaattgaagg aatgttttct taaccaaacg gatgaaactc tgagcaatgt tgaggtgttt     300
atgcaattaa tatatgacag cagtctttgt gatttatttt aactttctgc aagacctttg     360
gctcacagaa ctgcagggta tggtgagaaa ccaactacgg attgctgcaa accacacctt    420
ctctttctta tgtcttttta ctacaaacta caagacaatt gttgaaacct gctatacatg    480
tttattttaa taaattgatg gca                                             503

<210> SEQ ID NO 18
<211> LENGTH: 503
<212> TYPE: DNA
<213> ORGANISM: Human

<400> SEQUENCE: 18
gacagcggct tccttgatcc ttgccacccg cgactgaaca ccgacagcag cagcctcacc      60
atgaagttgc tgatggtcct catgctggcg gccctctccc agcactgcta cgcaggctct     120
ggctgcccct tattggagaa tgtgatttcc aagacaatca atccacaagt gtctaagact     180
gaatacaaag aacttcttca agagttcata gacgacaatg ccactacaaa tgccatagat     240
gaattgaagg aatgttttct taaccaaacg gatgaaactc tgagcaatgt tgaggtgttt     300
atgcaattaa tatatgacag cagtctttgt gatttatttt aactttctgc aagacctttg     360
gctcacagaa ctgcagggta tggtgagaaa ccaactacgg attgctgcaa accacacctt    420
ctctttctta tgtcttttta ctacaaacta caagacaatt gttgaaacct gctatacatg    480
tttattttaa taaattgatg gca                                             503

<210> SEQ ID NO 19
<211> LENGTH: 1793
<212> TYPE: DNA
<213> ORGANISM: Human

<400> SEQUENCE: 19
cgcgtccgcc ccgcgagcac agagcctcgc ctttgccgat ccgccgcccg tccacacccg      60
```

| | |
|---|---:|
| ccgccagctc accatggatg atgatatcgc cgcgctcgtc gtcgacaacg gctccggcat | 120 |
| gtgcaaggcc ggcttcgcgg gcgacgatgc ccccgggcc gtcttcccct ccatcgtggg | 180 |
| gcgcccagg caccagggcg tgatggtggg catgggtcag aaggattcct atgtgggcga | 240 |
| cgaggcccag agcaagagag gcatcctcac cctgaagtac cccatcgagc acggcatcgt | 300 |
| caccaactgg gacgcatgg agaaaatctg gcaccacacc ttctacaatg agctgcgtgt | 360 |
| ggctcccgag gagcaccccg tgctgctgac cgaggccccc ctgaacccca aggccaaccg | 420 |
| cgagaagatg acccagatca tgtttgagac cttcaacacc ccagccatgt acgttgctat | 480 |
| ccaggctgtg ctatccctgt acgcctctgg ccgtaccact ggcatcgtga tggactccgg | 540 |
| tgacggggtc acccacactg tgcccatcta cgaggggtat gccctccccc atgccatcct | 600 |
| gcgtctggac ctggctggcc gggacctgac tgactacctc atgaagatcc tcaccgagcg | 660 |
| cggctacagc ttcaccacca cggccgagcg ggaaatcgtg cgtgacatta aggagaagct | 720 |
| gtgctacgtc gccctggact cgagcaaga gatggccacg gctgcttcca gctcctccct | 780 |
| ggagaagagc tacgagctgc ctgacggcca ggtcatcacc attggcaatg agcggttccg | 840 |
| ctgccctgag gcactcttcc agccttcctt cctgggcatg gagtcctgtg catccacga | 900 |
| aactaccttc aactccatca tgaagtgtga cgtggacatc cgcaaagacc tgtacgccaa | 960 |
| cacagtgctg tctggcggca ccaccatgta ccctggcatt gccgacagga tgcagaagga | 1020 |
| gatcactgcc ctggcaccca gcacaatgaa gatcaagatc attgctcctc ctgagcgcaa | 1080 |
| gtactccgtg tggatcggcg gctccatcct ggcctcgctg tccaccttcc agcagatgtg | 1140 |
| gatcagcaag caggagtatg acgagtccgg cccctccatc gtccaccgca aatgcttcta | 1200 |
| ggcggactat gacttagttg cgttacaccc tttcttgaca aaacctaact tgcgcagaaa | 1260 |
| acaagatgag attggcatgg ctttatttgt tttttttgtt ttgttttggt ttttttttt | 1320 |
| tttttggctt gactcaggat ttaaaaactg gaacggtgaa ggtgacagca gtcggttgga | 1380 |
| gcgagcatcc cccaaagttc acaatgtggc cgaggacttt gattgcacat tgttgttttt | 1440 |
| ttaatagtca ttccaaatat gagatgcatt gttacaggaa gtcccttgcc atcctaaaag | 1500 |
| ccaccccact tctctctaag gagaatggcc cagtcctctc ccaagtccac acaggggagg | 1560 |
| tgatagcatt gctttcgtgt aaattatgta atgcaaaatt tttttaatct tcgccttaat | 1620 |
| acttttttat tttgttttat tttgaatgat gagccttcgt gcccccctt ccccttttt | 1680 |
| gtcccccaac ttgagatgta tgaaggcttt tggtctccct gggagtgggt ggaggcagcc | 1740 |
| agggcttacc tgtacactga cttgagacca gttgaataaa agtgcacacc tta | 1793 |

<210> SEQ ID NO 20
<211> LENGTH: 1377
<212> TYPE: DNA
<213> ORGANISM: Human

<400> SEQUENCE: 20

| | |
|---|---:|
| cacacagcct actttccaag cggagccatg tctggtaacg gcaatgcggc tgcaacggcg | 60 |
| gaagaaaaca gccaaagat gagagtgatt cgcgtgggta cccgcaagag ccagcttgct | 120 |
| cgcatacaga cggacagtgt ggtggcaaca ttgaaagcct cgtaccctgg cctgcagttt | 180 |
| gaaatcattg ctatgtccac cacaggggac aagattcttg atactgcact ctctaagatt | 240 |
| ggagagaaaa gcctgtttac caaggagctt gaacatgccc tggagaagaa tgaagtggac | 300 |
| ctggttgttc actccttgaa ggacctgccc actgtgcttc ctcctggctt caccatcgga | 360 |
| gccatctgca gcgggaaaa ccctcatgat gctgttgtct ttcacccaaa atttgttggg | 420 |

-continued

```
aagaccctag aaaccctgcc agagaagagt gtggtgggaa ccagctccct gcgaagagca     480
gcccagctgc agagaaagtt cccgcatctg agttcagga gtattcgggg aaacctcaac     540
acccggcttc ggaagctgga cgagcagcag gagttcagtg ccatcatcct agcaacagct     600
ggcctgcagc gcatgggctg gcacaaccgg gtggggcaga tcctgcaccc tgagaaatgc     660
atgtatgctg tgggccaggg ggccttgggc gtggaagtgc gagccaagga ccaggacatc     720
ttggatctgg tgggtgtgct gcacgatccc gagactctgc ttcgctgcat cgctgaaagg     780
gccttcctga ggcacctgga aggaggctgc agtgtgccag tagccgtgca tacagctatg     840
aaggatgggc aactgtacct gactggagga gtctggagtc tagacggctc agatagcata     900
caagagacca tgcaggctac catccatgtc cctgcccagc atgaagatgg ccctgaggat     960
gacccacagt tggtaggcat cactgctcgt aacattccac gagggcccca gttggctgcc    1020
cagaacttgg gcatcagcct ggccaacttg ttgctgagca aggagccaa aaacatcctg    1080 gatgttgcac ggcagcttaa cgatgcccat taactggttt gtggggcaca gatgcctggg    1140
ttgctgctgt ccagtgccta catcccgggc ctcagtgccc cattctcact gctatctggg    1200
gagtgattac cccgggagac tgaactgcag ggttcaagcc ttccagggat ttgcctcacc    1260
ttggggcctt gatgactgcc ttgcctcctc agtatgtggg ggcttcatct ctttagagaa    1320
gtccaagcaa cagcctttga atgtaaccaa tcctactaat aaaccagttc tgaaggt      1377
```

<210> SEQ ID NO 21
<211> LENGTH: 1524
<212> TYPE: DNA
<213> ORGANISM: Human

<400> SEQUENCE: 21

```
agcagacaga ggactctcat taaggaaggt gtcctgtgcc ctgaccctac aagatgccaa      60
gagaagatgc tcacttcatc tatggttacc ccaagaaggg gcacggccac tcttacacca     120
cggctgaaga ggccgctggg atcggcatcc tgacagtgat cctgggagtc ttactgctca     180
tcggctgttg gtattgtaga agacgaaatg gatacagagc cttgatggat aaaagtcttc     240
atgttggcac tcaatgtgcc ttaacaagaa gatgcccaca agaagggttt gatcatcggg     300
acagcaaagt gtctcttcaa gagaaaaact gtgaacctgt ggttcccaat gctccacctg     360
cttatgagaa actctctgca gaacagtcac caccacctta ttcaccttaa gagccagcga     420
gacacctgag acatgctgaa attatttctc tcacactttt gcttgaattt aatacagaca     480
tctaatgttc tccttggaa tggtgtagga aaaatgcaag ccatctctaa taataagtca     540
gtgttaaaat tttagtaggt ccgctagcag tactaatcat gtgaggaaat gatgagaaat     600
attaaattgg gaaaactcca tcaataaatg ttgcaatgca tgatactatc tgtgccagag     660
gtaatgttag taaatccatg gtgttatttt ctgagagaca gaattcaagt gggtattctg     720 ggccatcca atttctcttt acttgaaatt tggctaataa caaactagtc aggttttcga     780
accttgaccg acatgaactg tacacagaat tgttccagta ctatggagtg ctcacaaagg     840
atacttttac aggttaagac aaagggttga ctggcctatt tatctgatca agaacatgtc     900
agcaatgtct ctttgtgctc taaaattcta ttatactaca ataatatatt gtaaagatcc     960
tatagctctt ttttttgag atggagtttc gcttttgttg cccaggctgg agtgcaatgg    1020
cgcgatcttg gctcaccata acctccgcct cccaggttca gcaattctc ctgccttagc    1080 ctcctgagta gctgggatta caggcgtgcg ccactatgcc tgactaattt tgtagtttta    1140
```

-continued

```
gtagagacgg ggtttctcca tgttggtcag gctggtctca aactcctgac ctcaggtgat      1200
ctgcccgcct cagcctccca aagtgctgga attacaggcg tgagccacca cgcctggctg      1260
gatcctatat cttaggtaag acatataacg cagtctaatt acatttcact tcaaggctca      1320
atgctattct aactaatgac aagtattttc tactaaacca gaaattggta gaaggattta      1380
aataagtaaa agctactatg tactgcctta gtgctgatgc ctgtgtactg ccttaaatgt      1440
acctatggca atttagctct cttgggttcc caaatccctc tcacaagaat gtgcagaaga      1500
aatcataaag gatcagagat tctg                                             1524
```

<210> SEQ ID NO 22
<211> LENGTH: 2384
<212> TYPE: DNA
<213> ORGANISM: Human

<400> SEQUENCE: 22

```
tattgagttc ttcaaacatt gtagcctctt tatggtctct gagaaataac taccttaaac        60
ccataatctt taatacttcc taaactttct taataagaga agctctattc ctgacactac       120
ctctcatttg caaggtcaaa tcatcattag ttttgtagtc tattaactgg gtttgcttag       180
gtcaggcatt attattacta accttattgt taatattcta accataagaa ttaaactatt       240
aatggtgaat agagttttc actttaacat aggcctatcc cactggtggg atacgagcca       300
attcgaaaga aaagtcagtc atgtgctttt cagaggatga aagcttaaga taaagactaa       360
aagtgtttga tgctggaggt gggagtggta ttatataggt ctcagccaag acatgtgata       420
atcactgtag tagtagctgg aaagagaaat ctgtgactcc aattagccag ttcctgcaga       480
ccttgtgagg actagaggaa gaatgctcct ggctgttttg tactgcctgc tgtggagttt       540
ccagacctcc gctggccatt tccctagagc ctgtgtctcc tctaagaacc tgatggagaa       600
ggaatgctgt ccaccgtgga gcggggacag gagtccctgt ggccagcttt caggcagagg       660
ttcctgtcag aatatccttc tgtccaatgc accacttggg cctcaatttc ccttcacagg       720
ggtggatgac cggagtcgt ggccttccgt ctttttataat aggacctgcc agtgctctgg       780
caacttcatg ggattcaact gtggaaactg caagtttggc ttttggggac caaactgcac       840
agagagacga ctcttggtga gaagaaacat cttcgatttg agtgcccag agaaggacaa       900 attttttgcc tacctcactt tagcaaagca taccatcagc tcagactatg tcatccccat       960
agggacctat ggccaaatga aaatggatc aacacccatg tttaacgaca tcaatattta      1020
tgacctcttt gtctggatgc attattatgt gtcaatggat gcactgcttg ggggatctga      1080
aatctggaga gacattgatt ttgcccatga agcaccagct tttctgcctt ggcatagact      1140
cttcttgttg cggtgggaac aagaaatcca gaagctgaca ggagatgaaa acttcactat      1200
tccatattgg gactggcggg atgcagaaaa gtgtgacatt tgcacagatg agtacatggg      1260
aggtcagcac cccacaaatc ctaacttact cagcccagca tcattcttct cctcttggca      1320
gattgtctgt agccgattgg aggagtacaa cagccatcag tctttatgca atggaacgcc      1380
cgagggacct ttacggcgta atcctggaaa ccatgacaaa tccagaaccc caaggctccc      1440
ctcttcagct gatgtagaat tttgcctgag tttgacccaa tatgaatctg gttccatgga      1500
taaagctgcc aatttcagct ttagaaatac actggaagga tttgctagtc cacttactgg      1560
gatagcggat gcctctcaaa gcagcatgca caatgccttg cacatctata tgaatggaac      1620
aatgtcccag gtacagggat ctgccaacga tcctatcttc cttcttcacc atgcatttgt      1680
tgacagtatt tttgagcagt ggctccgaag gcaccgtcct cttcaagaag tttatccaga      1740
```

```
agccaatgca cccattggac ataaccggga atcctacatg gttcctttta taccactgta    1800
cagaaatggt gatttctttta tttcatccaa agatctgggc tatgactata gctatctaca   1860
agattcagac ccagactctt ttcaagacta cattaagtcc tatttggaac aagcgagtcg    1920
gatctggtca tggctccttg gggcggcgat ggtaggggcc gtcctcactg ccctgctggc    1980
agggcttgtg agcttgctgt gtcgtcacaa gagaaagcag cttcctgaag aaaagcagcc    2040
actcctcatg gagaaagagg attaccacag cttgtatcag agccatttat aaaaggctta    2100
ggcaatagag tagggccaaa aagcctgacc tcactctaac tcaaagtaat gtccaggttc    2160
ccagagaata tctgctggta tttttctgta aagaccattt gcaaaattgt aacctaatac    2220
aaagtgtagc cttcttccaa ctcaggtaga acacacctgt ctttgtcttg ctgttttcac    2280
tcagcccttt taacatttc ccctaagccc atatgtctaa ggaaaggatg ctatttggta    2340
atgaggaact gttatttgta tgtgaattaa agtgctctta tttt                    2384
```

```
<210> SEQ ID NO 23
<211> LENGTH: 30
<212> TYPE: DNA
<213> ORGANISM: Artificial
<220> FEATURE:
<223> OTHER INFORMATION: Artificial sequence is a Probe

<400> SEQUENCE: 23
cctgaggcac ctggaaggag gctgcagtgt                                     30

<210> SEQ ID NO 24
<211> LENGTH: 27
<212> TYPE: DNA
<213> ORGANISM: Artificial
<220> FEATURE:
<223> OTHER INFORMATION: Artificial sequence is a Probe

<400> SEQUENCE: 24
atcaaaaaac aagcatggcc tcacacc                                        27

<210> SEQ ID NO 25
<211> LENGTH: 22
<212> TYPE: DNA
<213> ORGANISM: Artificial
<220> FEATURE:
<223> OTHER INFORMATION: Artificial sequence is a Primer

<400> SEQUENCE: 25
ctgcttcgct gcatcgctga aa                                             22

<210> SEQ ID NO 26
<211> LENGTH: 22
<212> TYPE: DNA
<213> ORGANISM: Artificial
<220> FEATURE:
<223> OTHER INFORMATION: Artificial sequence is a Primer

<400> SEQUENCE: 26
cagactcctc cagtcaggta ca                                             22

<210> SEQ ID NO 27
<211> LENGTH: 21
<212> TYPE: DNA
<213> ORGANISM: Artificial
<220> FEATURE:
<223> OTHER INFORMATION: Artificial sequence is a Primer
```

```
<400> SEQUENCE: 27
gcttggtggt taaaacttac c                                              21

<210> SEQ ID NO 28
<211> LENGTH: 20
<212> TYPE: DNA
<213> ORGANISM: Artificial
<220> FEATURE:
<223> OTHER INFORMATION: Artificial sequence is a Primer

<400> SEQUENCE: 28
tgaacagttc tgttggtgta                                                20

<210> SEQ ID NO 29
<211> LENGTH: 27
<212> TYPE: DNA
<213> ORGANISM: Artificial
<220> FEATURE:
<223> OTHER INFORMATION: Artificial sequence is a Probe

<400> SEQUENCE: 29
ctgcctgcct atgtgacgac aatccgg                                        27

<210> SEQ ID NO 30
<211> LENGTH: 20
<212> TYPE: DNA
<213> ORGANISM: Artificial
<220> FEATURE:
<223> OTHER INFORMATION: Artificial sequence is a Primer
<220> FEATURE:
<221> NAME/KEY: misc_feature
<222> LOCATION: (213)..(213)
<223> OTHER INFORMATION: misc_feature is artificial primer

<400> SEQUENCE: 30
caattttggt ggagaacccg                                                20

<210> SEQ ID NO 31
<211> LENGTH: 20
<212> TYPE: DNA
<213> ORGANISM: Artificial
<220> FEATURE:
<223> OTHER INFORMATION: Artificial sequence is a Primer

<400> SEQUENCE: 31
gctgtcggag gtatatggtg                                                20

<210> SEQ ID NO 32
<211> LENGTH: 28
<212> TYPE: DNA
<213> ORGANISM: Artificial
<220> FEATURE:
<223> OTHER INFORMATION: Artificial sequence is a Probe

<400> SEQUENCE: 32
catttcagag agtaacatgg actacaca                                       28

<210> SEQ ID NO 33
<211> LENGTH: 21
<212> TYPE: DNA
<213> ORGANISM: Artificial
<220> FEATURE:
<223> OTHER INFORMATION: Artificial sequence is a Primer

<400> SEQUENCE: 33
gcaagtgcca atgatcagag g                                              21
```

```
<210> SEQ ID NO 34
<211> LENGTH: 23
<212> TYPE: DNA
<213> ORGANISM: Artificial
<220> FEATURE:
<223> OTHER INFORMATION: Artificial sequence is a Primer

<400> SEQUENCE: 34
atatagactc aggtatacac act                                               23

<210> SEQ ID NO 35
<211> LENGTH: 27
<212> TYPE: DNA
<213> ORGANISM: Artificial
<220> FEATURE:
<223> OTHER INFORMATION: Artificial sequence is a Probe

<400> SEQUENCE: 35
tcccatcaga atccaaacaa gaggaag                                           27
```